(12) United States Patent
Resch-Genger et al.

(10) Patent No.: US 7,947,502 B2
(45) Date of Patent: May 24, 2011

US007947502B2

(54) METHOD AND KIT FOR CALIBRATING A PHOTOLUMINESCENCE MEASUREMENT SYSTEM

(75) Inventors: Ute Resch-Genger, Berlin (DE); Dietmar Pfeifer, Berlin (DE); Christian Monte, Berlin (DE); Angelika Hoffmann, Berlin (DE); Pierre Nording, Gams SG (CH); Bernhard Schönenberger, Azmoos SG (CH); Katrin Hoffmann, Berlin (DE); Monika Spieles, Berlin (DE); Knut Rurack, Berlin (DE)

(73) Assignees: Sigma-Aldrich GmbH, Buchs (CH); BAM Bundesanstalt für Materialforschung und-prüefung, Berlin (DE)

( * ) Notice: Subject to any disclaimer, the term of this patent is extended or adjusted under 35 U.S.C. 154(b) by 0 days.

(21) Appl. No.: 12/729,614

(22) Filed: Mar. 23, 2010

(65) Prior Publication Data

US 2010/0219333 A1 Sep. 2, 2010

Related U.S. Application Data

(62) Division of application No. 11/223,202, filed on Sep. 9, 2005, now Pat. No. 7,713,741.

(30) Foreign Application Priority Data

Sep. 10, 2004 (DE) .......................... 10 2004 044 717

(51) Int. Cl.
*G01N 31/00* (2006.01)
*G01N 21/76* (2006.01)
*G01J 1/58* (2006.01)
*G01J 1/10* (2006.01)

(52) U.S. Cl. ............ 436/8; 436/164; 436/171; 436/172; 73/1.01; 702/22; 702/28; 250/252.1; 250/458.1; 422/82.05; 422/82.08; 422/430; 356/243.1

(58) Field of Classification Search ............... 436/8, 164, 436/171, 172; 73/1.01; 702/22, 27, 28, 32; 250/252.1, 458.1, 459.1; 422/61, 82.05, 422/82.08, 430; 356/243.1
See application file for complete search history.

(56) References Cited

U.S. PATENT DOCUMENTS

| 4,704,891 A | 11/1987 | Recktenwald et al. |
| 7,713,741 B2 * | 5/2010 | Resch-Genger et al. ......... 436/8 |
| 2006/0233668 A1 | 10/2006 | Resch-Gener et al. |

FOREIGN PATENT DOCUMENTS

| DE | 37 81 85 T2 | 4/1993 |
| DE | 195 15 821 C2 | 10/1996 |
| DE | 198 47 370 A1 | 4/2000 |
| DE | 102 00 865 A1 | 10/2002 |
| DE | 695 30 323 A1 | 2/2004 |

OTHER PUBLICATIONS

Pfeifer et al. Journal of Fluorescence, vol. 16, 2006, pp. 581-587.*
J.W. Hofstraat, et al.; "Correction of Fluorescence Spectra"; Applied Spectroscopy; vol. 48, No. 4, 1994, p. 436-447.
R.A. Velapoldi, et al.; Standard Reference Materials: A Fluorescence Standard Reference Material: Quinine Sulfate Dihydrate; Jan. 1980; U.S. Department of Commerce; pp. iii-115.
Resch-Genger et al. Journal of Fluorescence, vol. 15, No. 3, May 2005, pp. 315-336.
Resch-Genger et al. Journal of Fluoresecence, vol. 15, No. 3, May 2005, pp. 337-362.
J.A. Gardecki et al.; Set of Secondary Emission Standards for Calibration of the Spectral Responsivitiy in Emission Spectroscopy; Applied Spectroscopy, vol. 52, No. 9, 1998, pp. 1179-1189.

* cited by examiner

*Primary Examiner* — Maureen M Wallenhorst
(74) *Attorney, Agent, or Firm* — Norris McLaughlin & Marcus, P.A.

(57) ABSTRACT

The invention is directed to a method and a kit for calibrating a photoluminescence measurement system, in particular a fluorescence measurement system. The kit includes a number of fluorescence standards i and their corrected and certified fluorescence spectra $I_i(\lambda)$, whereby the fluorescence standards i are selected, so that their spectrally corrected fluorescence spectra $I_i(\lambda)$ cover a broad spectral range with high intensity. The standards are characterized by large halfwidths $FWHM_i$ of their bands of at least 1400 cm$^{-1}$. According to the method of the invention, partial correction functions $F_i(\lambda)$ are generated by forming the quotient of the measured fluorescence spectra $J_i(\lambda)$ and the corresponding corrected fluorescence spectra $I_i(\lambda)$, which are then combined to form a total correction function $F(\lambda)$ for a broad spectral range. The combination factors $\alpha_i$ are hereby computed by statistical averaging of consecutive partial correction functions $F_i(\lambda)$ over only a predefined, limited overlap region $\lambda_{i/i+1} \pm \Delta\lambda_{OL}$ about the mutual crossover wavelength $\lambda_{i/i+1}$.

9 Claims, 4 Drawing Sheets

METHOD AND KIT FOR CALIBRATING A PHOTOLUMINESCENCE MEASUREMENT SYSTEM

Figure 1:
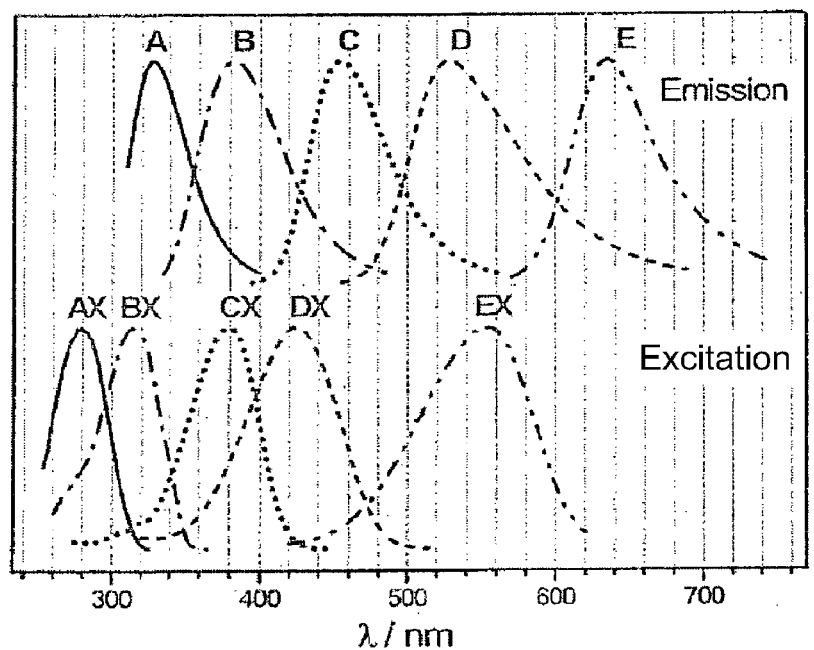

This is a divisional application of U.S. Ser. No. 11/223,202, which was filed on Sep. 9, 2005, now U.S. Pat. No. 7,713,741 issued on May. 11, 2010.

The invention relates to a method and a kit for calibrating a photoluminescence measurement system, in particular a fluorescence measurement system. The invention also relates to the use of the kit as well as the use of selected chemical compounds as fluorescence standards for calibrating photoluminescence measurement systems.

Each luminescence measurement technique provides measurement data with analyte-specific and device-specific contributions. The undesirable, device-specific contributions reflect the wavelength- and polarization-dependence of device components of the employed measurement device. These dependencies are caused, in particular, by the optical components in the excitation and emission channel of the device, the excitation light source, and the employed detection systems. A comparison between luminescence data from different devices and laboratories, measurements reflecting device aging, the demand for traceability of luminescence data to radiometric primary standards (according to the general requirement in EN ISO/IEC 17025) as well as many quantitative fluorescence results, the determination of relative fluorescence quantum yields and the optimization of luminescence methods require the determination of these device-specific contributions. This applies, in particular, to a comparative evaluation of spectrally shifted luminescence profiles or to emission measurements at different excitation wavelengths.

Photoluminescence measurement devices generally have an excitation channel which can include an excitation light source and a wavelength-selective optical component, and an emission channel, which is typically arranged perpendicular to the optical path of the excitation light and is used to record the light (photoluminescence) emitted by the chromophore located in the sample space after light absorption. Frequently, a defined fraction of the excitation light is coupled with a beam splitter into a reference channel, which includes an optical component, such as a mirror or a scatterer and a (reference) detector. The reference channel is used to record the actual excitation light intensity at the excitation wavelength so as to capture short-term variations in the intensity of the excitation light. The aforementioned device-specific contributions to the fluorescence signal can be determined by determining so-called correction functions, which describe the wavelength- and polarization-dependence of these effects for the emission and excitation channel of the corresponding device. The correction functions are determined independent of each other. The emission correction function includes the wavelength- and polarization-dependent transmission efficiency of the optical components in the emission channel and the wavelength- and polarization-dependent spectral sensitivity of the employed detection system. The excitation correction function describes the wavelength-dependent spectral radiance of the excitation light source and the wavelength- and polarization-dependent transmission efficiency of the optical components in the excitation channel.

It is known to employ certified physical transfer standards for determining the device-specific effects. Typically, certified receiver standards are used for calibrating the excitation channel, and certified standard lamps are used for calibrating the emission channel. Disadvantageously, the use of physical transfer standards requires from the user a thorough optical understanding of the application, expensive recalibrations, changes in the spectral radiance of standard lamps which depend on their operating life, and for an emission correction with standard lamps the different emission characteristics of lamp and sample, and the differences in spectral radiance between the transfer standard and a typical luminescent sample of potentially at least three orders of magnitude. This can produce erroneous and substandard correction functions and is also complex and expensive. Physical transfer standards are also in many cases not suitable for the calibration of simple, compact photoluminescence measurement systems.

So-called quantum counters can also be used for the excitation correction. These are highly concentrated dye solutions, which completely absorb the incident light quanta and emit with a wavelength-independent fluorescence quantum yield. Measurement data obtained with quantum counters are quite dependent on concentration and geometry, and are also susceptive to polarization effects. Standardized calibration methods with defined concentrations, in combination with defined measurement geometries, are not available for quantum counters.

Also known are so-called fluorescence standards, which are typically based on the photoluminescence of a chemical compound. Spectral fluorescence standards or so-called emission and excitation standards with known and corrected (for device-specific effects) emission and/or excitation spectra can be used in a device calibration for determining the spectral characteristics of photoluminescence measurement systems. Such fluorescence standards are employed in various forms, in particular in the form of solutions or embedded in solid polymer or glass matrices. Fluorescence standards, in particular in the form of solutions, advantageously have a luminescence intensity and emission characteristics that are very similar to that of the luminescence samples to be investigated. Fluorescence standards therefore enable the (spectral) calibration under the conditions typical for sample measurements. The fluorescence standards can be measured in many different types of devices, formats and measurement geometries and are therefore also suitable for the calibration of fluorescence measurement systems with particular sample geometries or sample formats, for example in micro-cuvettes, micro-titer plates, or cryostat systems. Only fluorescence standards enable calibration in the same cuvette or measurement arrangement used for the actual sample measurement, so that optimal calibration results can be obtained. One problem with fluorescence standards is the large number of material and luminescence properties to be defined. A prerequisite for the suitability of a transfer standard is the complete characterization of all application-specific properties, including the employed methods, and information about the measurement uncertainty, as well as a sufficient long-term stability in the pure solid state and in solution, or when embedded in a matrix.

The technical literature discusses in detail many recommendations regarding fluorescence standards, which also includes emission and excitation standards and fluorescence quantum yield standards. Quinine sulfate dihydrate (SRM936) is so far the only emission standard whose corrected emission spectrum is certified by a government agency, in this case by the National Institute for Standards and Technology (NIST, USA) using a traceably characterized reference fluorometer with a known measurement uncertainty (R. A. Velapoldi, K. D. Mielenz, NBS Spec. Publ. 1980, 260-264, PB 80132046, Springfield, Va.). Information regarding the dye purity, the calibration of the employed spectrometer, the employed measurement parameters, and the measurement uncertainty is available only for this standard.

The spectral range where fluorescence standards can be used for calibration is limited by the position and width of the fluorescence bands. Only the band at the longest wavelength should be used for excitation standards. The emission standard quinine sulfate covers only the spectral range from approximately 400 to 550 nm. Several chromophores having matching fluorescence spectra must be combined for calibrating a photoluminescence measurement system over the entire UV/vis/NIR spectral range. However, so far only a few exemplary standard combinations are known. For example, a combination (no longer commercially available) of emission standards is known which includes fluorophore-containing polymeric foils with NIST-certified emission spectra (A. Thommpson, K. L. Eckerle, SPIE 1989, 1054, 20, J. W. Hofstraat & M. J. Latuhidin, Appl. Spectrosc. 1994, 48, 436). The system requires a defined measurement geometry, the use of polarizers, and measurement of the luminescence in Front-Face geometry, and is therefore not suitable for the calibration of simple measurement systems. The measurement conditions are also different from typical conditions for liquid samples. Combining the various partial correction functions to a total correction function is not described.

Fluorophore-containing polymethyl-methacrylate (PMMA) blocks in the form of cuvettes are also known as emission and excitation standards. The employed fluorophores typically have strongly structured emission and excitation spectra as well as steeply ascending flanks, which makes the fluorescence profile dependent on the monochromator bandpass and increases the calibration uncertainty. Uncertainties in the wavelength accuracy also cause serious errors in the fluorescence intensity. The spectra are not traceable; they do not match and cannot be combined to a total correction function.

Other known dye solutions of different fluorophores frequently have a problem with narrow, steeply rising emission bands and an insufficient spectral separation between absorption and emission bands. They are therefore unsuitable as emission standards. Several substances have inadequate photo stability and form under typical excitation and measurement conditions photo products with inherent spectral contributions. Many employed substances have an exceedingly large fluorescence anisotropy, which represents an additional error source in the calibration and requires the use of polarizers. In general, the aforedescribed spectra are not traceable, information about the measurement uncertainty is lacking, and only in exceptional cases (quinine sulfate dihydrate) are the spectra certified by an authorized agency. Frequently, the characterization of the application-relevant spectroscopic properties is also incomplete, and information about the dye purity is lacking in most cases.

A statistical solution trial for linking partial correction functions of different dye standards to a total correction function by applying counting rate statistics (Poisson statistics) is described by J. A. Gardecki and M. Maroncelli (Appl. Spectrosc. 1998, 52, 1179). The fluorescence standards employed therein have sometimes the aforementioned deficiencies, such as steep and structured bands (α-NPO), inadequate photo stability in solution (tryptophane, coumarine 102) or an exceedingly high fluorescence anisotropy (LDS 751). Because the employed mathematical solution trial is based on counting statistics, the method is designed only for devices operating in a photo counting mode and hence with very large absolute numbers. Application of the counting statistics in devices operating in analog mode, where the intensities are represented by significantly smaller numerical values, causes significant artifacts in the so-called correction functions. The method is also designed for use by experienced fluorescence spectroscopists. Disadvantageously with this method, the emission spectra provided by many fluorometers, as related to the reference light (forming the quotient of emission and reference), can also produce artifacts in the total correction function, when the partial correction curves of the individual emission standards are combined with each other. These artifacts can occur when only small or slightly negative values, as in the fluorescence sidebands, enter the calculation after correcting for blank values.

In summary, it can be stated that presently no calibration system exists which enables a reliable, traceable and easily manageable calibration over the entire spectral range of a photoluminescence measurement system, by using dye standards with a known uncertainty in their application-relevant fluorescence properties, which satisfy all requirements for a reproducible and traceable calibration. It is therefore an object of the present invention to provide a comprehensive calibration system using fluorescence standards, and a calibration method, which allows a simple and reproducible calibration that can be traced to primary radiometric standards (black body; cryo-radiometer), and which enables a reliable calibration of a photoluminescence measurement system over an extended spectral range.

The object is solved by a kit with fluorescence standards (emission standards and/or excitation standards) and by a method having the features of the independent claims.

The method according to the invention for calibrating a photoluminescence measurement system, in particular a fluorescence measurement system, includes the steps of (a) measuring fluorescence spectra $J_i(\lambda)$ of a plurality of fluorescence standards i with the photoluminescence measurement system to be calibrated, wherein the fluorescence standards i are selected, so that their combined spectrally corrected fluorescence spectra $I_i(\lambda)$ cover a predefined spectral range in such a way, that the fluorescence bands of the corrected, sequentially arranged fluorescence spectra $I_i(\lambda)$ have at least a minimum predefined intensity at their crossover wavelengths $\lambda_{i/i+1}$;

(b) calculating combination factors $\alpha_i$ through statistical averaging of consecutive partial correction functions $F_i(\lambda)$, wherein the partial correction functions $F_i(\lambda)$ are formed by forming the quotient of the measured fluorescence spectra $J_i(\lambda)$ and the corresponding corrected fluorescence spectra $I_i(\lambda)$ of the fluorescence standards i, and wherein the statistical averaging takes place over a predefined, limited overlap region $\lambda_{i/i+1} \pm \Delta\lambda_{OL}$ about the mutual crossover wavelengths $\lambda_{i/i+1}$; and (c) determining a total correction function $F(\lambda)$ for the predefined spectral range by statistical combination of the partial correction functions $F_i(\lambda)$, which are weighted according to the combination factors $\alpha_i$.

In the context of the present invention, the term corrected fluorescence spectrum refers to an emission or excitation spectrum obtained in a traceably calibrated luminescence measurement system under defined measurement conditions. The corrected fluorescence spectrum is device-independent as a result of the correction of the device-specific contributions of the calibrated measurement system. Preferably, the spectrum is certified by an authorized agency (for example NIST).

The method of the invention is different from conventional approaches (Gardecki and Maroncelli, Appl. Spectrosc. 1998, 52, 1179) mainly in that statistical averaging and/or weighting of the partial correction functions for determining the combination factors $\alpha_i$, on which the determination of the total correction function depends, is performed exclusively for defined overlap regions of the partial correction functions, i.e., only for a limited narrow spectral environment of the various crossover wavelengths. With the matching dye standards according to the invention, which have a minimum relative intensity at the respective crossover wavelengths of their fluorescence bands, advantageously only spectral contributions of the initial base spectra with a relatively high-intensity and hence low error contributions are consider in the statistical analysis. In particular, non-ideal measurement spectra and their partial correction functions can also be used with the method of the invention. For example, the present method also produces a smooth and continuous total correction function for those measurement spectra which, after correcting for blank values (subtracting the buffer spectrum), have negative intensity values in the region of the spectral flanks.

According to the invention, the overlap region about the crossover wavelengths is at most 12 nm in an adjacent region on both sides of the respective crossover point. More particularly, statistical averaging is performed over a range of ±10 nm, preferably of only ±8 nm, about each crossover wavelengths. This feature, together with the required minimum intensities of the spectra at the crossover wavelengths, guarantees that only relatively high intensities are applied in the statistical analysis, thereby eliminating artifacts in the correction functions.

Moreover, the relative minimum intensity to be maintained at each of the individual crossover wavelengths is at least 20% of the maximum intensity of the fluorescence bands. Less erroneous results are obtained with an intensity of at least 25%, preferably of at least 30% of the maximum in-band intensity. In actual applications, these intensities are approximately 40% of the maximum in-band intensity. The aforementioned values apply to the UV/vis spectral range with $\lambda \leq 700$ nm. Because the NIR range with $\lambda > 700$ nm generally has lower quantum yields and therefore also lower absolute intensities, lower minimum intensities at the crossover points of at least 10%, in particular of at approximately 12%, of the maximum intensity of the respective flanking bands can be tolerated in this region. In view of the limited overlap region where the combination factors $\alpha_i$ are statistically determined, only intensities of the corrected or measured (normalized) spectra of at least 10%, in particular of at least 15%, preferably of at least 20%, relative to the maximum intensities of the corresponding spectra enter in the statistical analysis at least in the UV/vis region.

According to a particular advantageous embodiment of the method, the functional dependence of the total correction function in a predefined, limited spectral combination range $\lambda_{i/i+1} \pm \Delta\lambda_{LK}$ about the crossover wavelengths, which is narrower than the aforementioned overlap region $\lambda_{i/i+1} \pm \Delta\lambda_{OL}$, is calculated through statistical averaging of the weighted, consecutive partial correction functions. On the other hand, the functional dependence of the total correction function outside the predefined combination region about the crossover wavelengths corresponds to the functional dependence of the weighted, but not averaged, partial correction functions. Advantageously, the limited combination region about the crossover wavelengths is very narrow, in particular not more than $\lambda_{i/i+1} \pm 5$ nm, more particularly ±2 nm. Most preferably, the combination region includes only the corresponding crossover point itself. In other words, the total correction function is composed of the weighted partial correction functions, whereby the weighted partial correction functions are averaged only at the crossover wavelengths. As a result, the total correction function is formed only from regions of high luminescence intensity in the underlying measured and corrected partial spectra. Intensities below the minimum intensities required at the crossover points are mostly disregarded. Excluding those spectral segments that have a low luminescence intensity from the average values results in smooth total correction functions with a minimum measurement uncertainty.

According to an advantageous embodiment of the method, the total correction function is formed over a predefined spectral range which covers at least in part the UV/vis/NIR spectral range. This predefined spectral range extends for the emission correction from 310 to 730 nm, in particular from 300 to 950 nm, and for the excitation correction of 250 to 630 nm, in particular from 240 to 900 nm. Taking into account the requirements according to the invention for the dye standards, this requires a combination of between 5 and 7 dyes.

According to another advantageous embodiment of the invention, a statistical, wavelength-dependent uncertainty for the device characteristics and, optionally, also for the fluorescence measurements for the predefined spectral range of the total correction function can be calculated by a user. This requires knowledge of the wavelength-dependent measurement uncertainty contributions for each corrected dye fluorescence spectrum. For example, the user can determine the contribution of the device-specific measurement uncertainty (standard deviation) from several repeat measurements (e.g., $N \geq 7$) of the dye spectra. A total measurement uncertainty contribution for the photoluminescence measurement system to be calibrated can then be generated from the aforementioned wavelength-dependent measurement uncertainty contributions for the corrected spectra of the dyes and from the repeat standard deviation.

The kit according to the invention, which may include a set of emission and excitation standards, for traceable calibration of the photoluminescence system, in particular a fluorescence measurement system, includes the following components:

a plurality of fluorescence standards i, and corrected fluorescence spectra $I_i(\lambda)$ of the fluorescence standards i in computer-readable form and/or a reference to an Internet page, from which the corrected fluorescence spectra $I_i(\lambda)$ can be downloaded, wherein the fluorescence standards i are selected so that their combined spectrally corrected fluorescence spectra $I_i(\lambda)$ cover a predefined spectral range in such a way, that fluorescence bands of the corrected, consecutive fluorescence spectra $I_i(\lambda)$ have in the vis/NIR spectral range with $\lambda \leq 700$ nm at least a minimum predefined intensity at their overlapping wavelengths $\lambda_{i/i+1}$ of at least 20% of the corresponding maximum in-band intensity, and (in the same spectral range) their fluorescence bands have a respective half-width (FWHM) of at least 1400 cm$^{-1}$.

The composition of the kit(s) according to the invention enables a user to reliably, reproducibly and cost-effectively calibrate the measurement system over a wide spectral range (310 to 730 nm, in particular from 300 to 950 nm for the emission correction, and from 250 to 630 nm, in particular from 240 to 900 nm for the excitation correction). In particular, matching the individual fluorescence standards according to the invention, i.e., their half-widths as well as the required minimum intensity at the crossover wavelengths, makes it possible to generate a total correction functions for the device with a quality that has been unattainable to date.

According to a preferred embodiment of the invention, the kit can include a program algorithm for computing partial correction functions $F_i(\lambda)$ which executes the method steps of the aforedescribed method of the invention and/or a reference to an Internet page, from which the algorithm can be downloaded.

Advantageously, the kit can include for each corrected fluorescence spectrum a device-independent, spectral measurement uncertainty curve in computer-readable form. Optionally or in addition, a reference to an Internet page can be provided, from which the measurement data together with the spectral measurement uncertainty curves can be downloaded. With the latter, a total measurement uncertainty curve can be generated for the total correction function, so that the wavelength-dependent measurement uncertainty of the luminescence measurement system to be calibrated can be determined.

The kit may further include instructions for using the kit components and/or a reference to an Internet page, from which the instructions can be downloaded. The information can include, for example, information relating to the measurement conditions and the device settings and the like.

The fluorescence standards of the kit are measured in solution, because calibrations can then be performed under routine measurement conditions. In principle, the kit may contain the dyes in solid form or in form of prepared solutions. The kit may also include the solvents to be used, whereby preferably the same high-purity solvent is used with all transfers standards.

In additional embodiments of the invention, all fluorescence standards not only satisfy the required minimum intensity of the corrected fluorescence spectra at their respective crossover wavelengths in the UV/vis spectral range of at least 20%, in particular of at least 25%, preferably all the at least 30% of the maximum intensity of the luminescence bands (in the NIR range at least 10%, in particular at least 12%), and the required minimum half-width, which is in particular at least 1600 cm$^{-1}$, preferably at least 2000 cm$^{-1}$, and ideally at least 2400 cm$^{-1}$ (above 700 nm 1200 cm$^{-1}$, in particular 1400 cm$^{-1}$), but also satisfy the requirements described below. According to a particularly advantageous embodiment of the invention, all dye standards are selected so that their fluorescence bands have a smooth and unstructured curve shape, i.e., with a spectral resolution of 1 nm, the bands have only one maximum, no shoulders, and a continuous band waveform. Like the required minimum half-width associated with a small slope at the flanks of the bands, the unstructured and smooth shape of the bands also guarantees that the measured spectra are independent of the measurement conditions and the device features and/or the parameter settings of the employed spectrometer, in particular the monochromator bandpass and slit width of the measurement channel. The band characteristics of the invention therefore increase the calibration reliability.

In addition, the provided fluorescence standards have a purity of at least 98%, in particular of at least 99.5%. The overlap of excitation and emission bands of the dye standards is small. In particular, the spectral separation between absorption and emission bands is at least 2000 cm$^{-1}$, in particular of at least 2400 cm$^{-1}$, and ideally at least 2800 cm$^{-1}$. The anisotropy of the fluorescence of the dye standards in a temperature range of 20° C. to 30° C. and in the solvent to be used is in the UV/vis spectral range with $\lambda \leq 700$ nm at most 0.05 and preferably at most 0.04, and in the NIR spectral range at most 0.07 and preferably at most 0.06. Additional error sources in the calibration can be eliminated if the fluorescence spectra of the proposed dye standards have only a small temperature dependence in the temperature range of 20° C. to 30° C. The dye standards are further characterized by a high thermal and photo-chemical stability of the pure substances and also of their solutions. Finally, the dyes do not form photo products under measurement and excitation conditions typical for static photoluminescence measurements. In particular, they show a maximum of 10%, preferably a maximum of 2%, decrease of the fluorescence bands after a five-hour irradiation with light from a 100 watt xenon high-pressure lamp in the range of the longest wavelength absorption maximum at a width of the bandpass of approximately 15 nm, so that the thermal and photo-chemical stability is sufficient for the planned applications. In particular, the totality of the aforementioned spectroscopic and photo-chemical properties of the fluorescence standards guarantees a high calibration reliability and traceability according to EN ISI/IEC 17025.

The kit can include a number of different emission standards and their spectrally corrected emission spectra for generating a total correction function for the emission channel (emission correction function), as well as a number of different excitation standards and their spectrally corrected excitation spectra for generating a total correction function for the excitation channel (excitation correction function). The kit preferably includes both emission and excitation standards as well and their spectrally corrected emission and excitation spectra in electronic form on a data carrier or downloadable via the Internet.

More particularly, a set of preferred emission standards include compound selected from the group consisting of biphenyl, naphthalene, coumarine, oxazin, merocyanin, hemicyanin and styryl derivates. Excitation standards are preferably selected from the group consisting of biphenyl, terphenyl, oxadizol, coumarine, oxazin, merocyanin, hemicyanin and styryl derivates. In the following, several explicit emission and/or excitation standards are listed which satisfy the aforedescribed criteria.

A first preferred emission and/or excitation standard is a biphenyl derivate according to the general formula

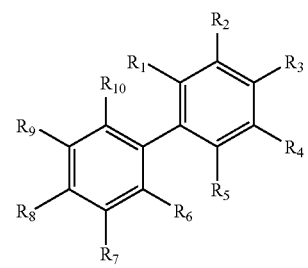

(1)

wherein the moieties $R_1$ to $R_{10}$ independently represent a hydrogen moiety, an alkyl or alkoxy moiety, or partially in combination with each other an anellated, saturated hetero- or homo-nuclear ring. Preferably, $R_1$ and $R_6$ each represent an alkoxy moiety, and the remaining moieties independently represent a hydrogen or an alkyl moiety, wherein the alkoxy and alkyl groups independently are cyclic or acyclic, branched or linear. Most preferably, $R_1$ and $R_6$ each represent a mesoxy moiety, and the other moieties each represent a hydrogen moiety. This compound is preferably used as an emission standard and has, for example, in ethanol an emission band from 290 to 410 nm at an excitation wavelength of 280 nm. The half-width is approximately 4250 cm$^{-1}$ and the separation between excitation and emission maxima approximately 5410 cm$^{-1}$.

A second preferred emission and/or excitation standard is a naphthalene derivate having the general formula 2

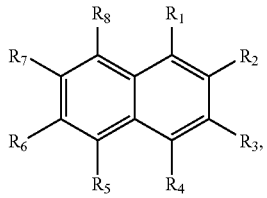
(2)

wherein the moieties $R_1$ to $R_8$ independent from each represent a hydrogen or alkoxy moiety, or partially in combination with each other an anellated, saturated, hetero- or homo-nuclear ring. Preferably, at least one of the two naphthalene rings is substituted by two alkoxy moieties in a minor-symmetric position (for example, $R_1$ and $R_4$ and/or $R_2$ and $R_3$), with the remaining moieties each being hydrogen. The alkoxy groups are acyclic, branched or linear, and do not have hydrogen moieties in β-position relative to the ether oxygen atom. Most preferably, $R_1$ and $R_4$ independently are a methoxy or neopentyloxy moiety, and the other moieties are each hydrogen moieties. This compounds is preferably used as an emission standard and have, for example, in ethanol an emission band from approximately 330 to 500 nm at an excitation wavelength of 320 nm. The half-width is approximately 4400 cm$^{-1}$ and the separation between excitation and emission maxima approximately 4930 cm$^{-1}$.

A third preferred emission and/or excitation standard is a coumarine derivate having the general formula 3

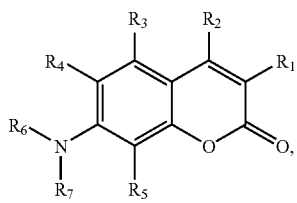
(3)

wherein the moieties $R_1$ to $R_7$ independently represent a hydrogen moiety or an unsubstituted or a substituted alkyl moiety, or partially in combination with each other an anellated, saturated homo-nuclear ring. $R_1$ and $R_2$ independently represent a hydrogen moiety or an unsubstituted or a substituted alkyl moiety, or an anellated, saturated homo-nuclear ring, $R_3$ to $R_5$ each a hydrogen moiety, and $R_6$ and $R_7$ independently a hydrogen moiety or an alkyl moiety. Preferably, $R_1$ to $R_5$ each represent a hydrogen moiety and $R_6$ and $R_7$ each an ethyl group. This compound is used as an emission and/or excitation standard and has, for example, in ethanol an emission band at approximately 400 to 600 nm at an excitation wavelength of 380 nm, as well as an excitation band of 325 to 430 nm at a detection wavelength of 460 nm. The half-width of the emission band is approximately 2850 cm$^{-1}$ and the separation between excitation and emission maxima approximately 4340 cm$^{-1}$. The excitation band has a half-width of approximately 3780 cm$^{-1}$.

A fourth preferred emission and/or excitation standard is a coumarine derivate having the general formula 4

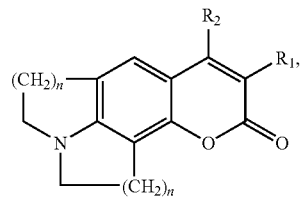
(4)

wherein the moieties $R_1$ and $R_2$ independently represent a hydrogen moiety or an unsubstituted or a substituted alkyl moiety, or in combination with each other an anellated, saturated homo-nuclear ring, with n=1 or 2. Preferably, $R_1$ represents a hydrogen and $R_2$ an unsubstituted or a substituted alkyl moiety, with n=1 or 2. Most preferably, $R_1$ is a hydrogen moiety and $R_2$ a trifluoromethyl moiety, with n=2. This compound is used as an emission and/or excitation standard and has, for example, in ethanol an emission band at approximately 460 to 700 nm at an excitation wavelength of 420 nm, as well as an excitation band of 330 to 490 nm at a detection wavelength of 530 nm. The half-width of the emission band is approximately 2890 cm$^{-1}$ and the separation between excitation and emission maxima approximately 4940 cm$^{-1}$. The excitation band has a half-width of approximately 4010 cm$^{-1}$.

A fifth emission and/or excitation standard is an oxazin derivate, in particular a 3H-phenoxazin-5-on derivate having the general formula 5

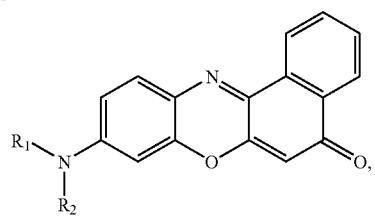
(5)

wherein the moieties $R_1$ and $R_2$ independently represent an unsubstituted or a substituted alkyl moiety. Preferably, $R_1$ and $R_2$ each represent an unsubstituted linear alkyl moiety, in particular an ethyl moiety. The compound is used as an emission and/or excitation standard and has, for example, in ethanol an emission band at approximately 570 to 750 nm at an excitation wavelength of 550 nm, as well as an excitation band of 440 to 630 nm at a detection wavelength of 630 nm. The half-width of the emission bands is approximately 1630 cm$^{-1}$ and the separation between excitation and emission maxima approximately 2440 cm$^{-1}$. The excitation band has a half-width of approximately 2960 cm$^{-1}$.

A sixth emission and/or excitation standard is a styryl derivate having the general formula 6

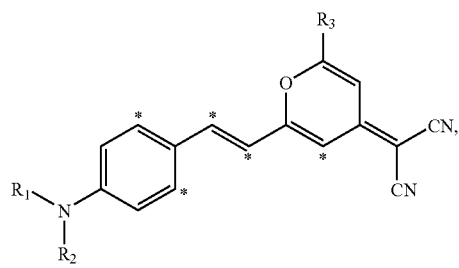
(6)

wherein $R_1$ and $R_2$ independently represent an unsubstituted or a substituted alkyl moiety, $R_3$ a hydrogen moiety or an unsubstituted or a substituted alkyl moiety. The C atoms designated with an asterisk can be independently bridged by a saturated C5 or C6 ring, as long as they are in a relative 1,3-position. Preferably, $R_1$ to $R_3$ are each a methyl moiety, and no bridging is present. This compound is preferably used as an emission standard and has, for example, in ethanol an emission band at approximately 530 to 750 nm at an excitation wavelength of 460 nm. The half-width of the emission band in acetone is 2323 cm$^{-1}$ and the separation between excitation ($\lambda_{ex}$=462 nm) and emission maxima ($\lambda_{max}$=626 nm) is 5670 cm$^{-1}$.

An additional emission and/or excitation standard is a styryl derivate, in particular a hemicyanin derivate, having the general formula 7

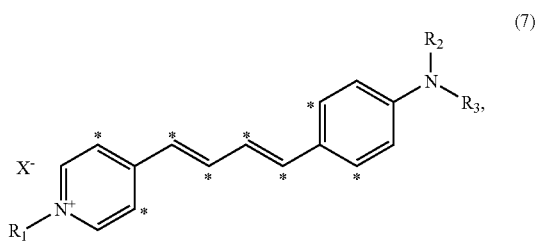

(7)

wherein $R_1$ to $R_3$ independently represent an unsubstituted or a substituted alkyl moiety and X$^-$ an arbitrary anion. The C atoms designated with an asterisk can be independently bridged by a saturated C5 or C6 ring, as long as they are in a relative 1,3-position. Preferably, $R_1$ is an ethyl moiety, $R_2$ and $R_3$ are each a methyl moiety, and X$^-$ a perchlorate anion, and no bridging is present. This compound is preferably used as an emission standard and has an emission band at approximately 600 to 800 nm at an excitation wavelength of 500 nm. The half-width of the emission band in acetone is 2808 cm$^{-1}$ and the separation between excitation ($\lambda_{ex}$=492 nm) and emission maxima ($\lambda_{max}$=719 nm) is 6417 cm$^{-1}$.

Another emission and/or excitation standard is a styryl derivate, in particular a hemicyanin derivate, having the general formula 8

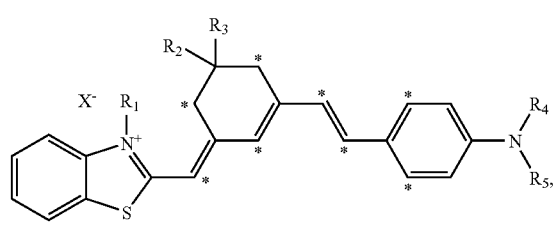

(8)

wherein $R_1$ to $R_5$ independently represent a hydrogen moiety or an unsubstituted or a substituted alkyl moiety and X$^-$ an arbitrary anion. The C atoms designated with an asterisk independently can be bridged by a saturated C5 or C6 ring, as long as they are in a relative 1,3-position. Preferably, $R_1$ to $R_5$ are each a methyl group and X$^-$ a perchlorate anion.

This compound is preferably used as an emission standard and has an emission band at approximately 700 to 920 nm at an excitation wavelength of 580 nm. The half-width of the emission band in acetone is 1460 cm$^{-1}$ and the separation between excitation ($\lambda_{ex}$=564 nm) and emission maxima ($\lambda_{max}$=810 nm) is 5380 cm$^{-1}$.

Another preferred emission and/or excitation standard is p-terphenyl having the general formula 9

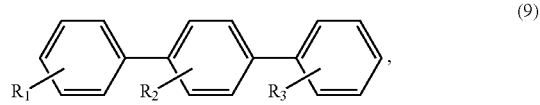

(9)

wherein $R_1$ to $R_3$ independently represent hydrogen, or an alkyl or alkoxy moiety, preferably however hydrogen. The compound is preferably used as an excitation standard and has an excitation band, for example in ethanol, at approximately 240 to 320 nm if the fluorescence is detected at 335 nm. The half-width of the excitation band is 5580 cm$^{-1}$.

Another preferred emission and/or excitation standard is a 1,3,4-oxadiazol derivate having the general formula 10

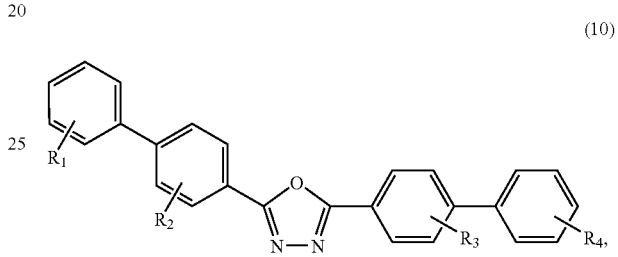

(10)

wherein $R_1$ to $R_4$ independently represent hydrogen, or an alkyl or alkoxy moiety, preferably however hydrogen. This compound is preferably used as an excitation standard and has an excitation band, for example in acetonitrile, at approximately 275 to 350 nm and an emission maximum at about 373 nm. The half-width of the excitation band is 4880 cm$^{-1}$.

According to a preferred embodiment, a kit includes a set of emission standards, which includes fluorescence emission standards according to each of the general formulas 1 to 5. Such kit covers the spectral range of approximately 310 to 730 nm In addition, the calibration kit can include at least one additional emission standard, selected from the general formulas 6, 7 and 8, for the emission channel, whereby a total correction function for the range from approximately 300 to 950 nm can be generated.

In particular preferred kit for generating a total correction function for the excitation channel includes a set of excitation standards, with the set including excitation standards according to each of the general formulas 3, 4, 5, 9 and 10.

None of the compounds of the general formulas 1, 2, and 5 to 10 have been used to date as fluorescence standards (emission and/or excitation standards), in particular not in the context of matching dye sets.

The kit of the invention and/or its dye standards can not only be used for the aforedescribed spectral calibration of photoluminescence measurement devices, but also as fluorescence quantum yield standards for determining relative fluorescence quantum yields in the UV/vis/NIR spectral range, i.e., for a quantitative calibration of the intensities. The fluorescence quantum yield is predefined as the ratio between the number of photons emitted by a sample and the number of photons absorbed by the sample. The kit and/or its dye standards may also be used to determine the linear region of a detection system of a photoluminescence measurement system. A detector range is hereby determined where the indicated intensity increases linearly with the incident intensity, i.e., where a reliable quantitative statement about a concentration of a chromophore in the probe is possible.

Additional advantageous embodiment of the invention are recited in the other dependent claims.

Figure 2:
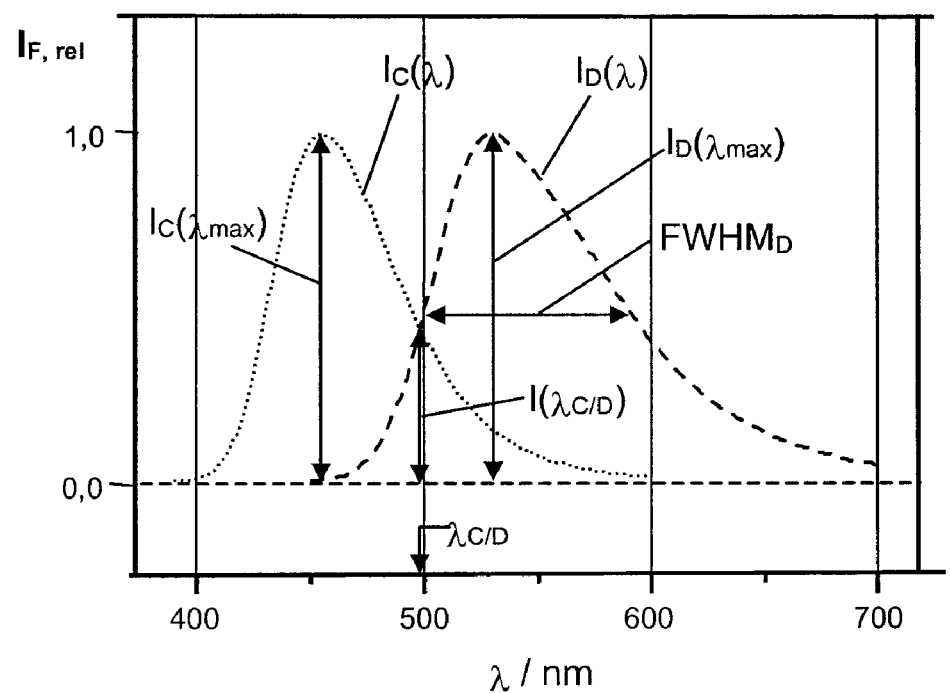
Figure 3:
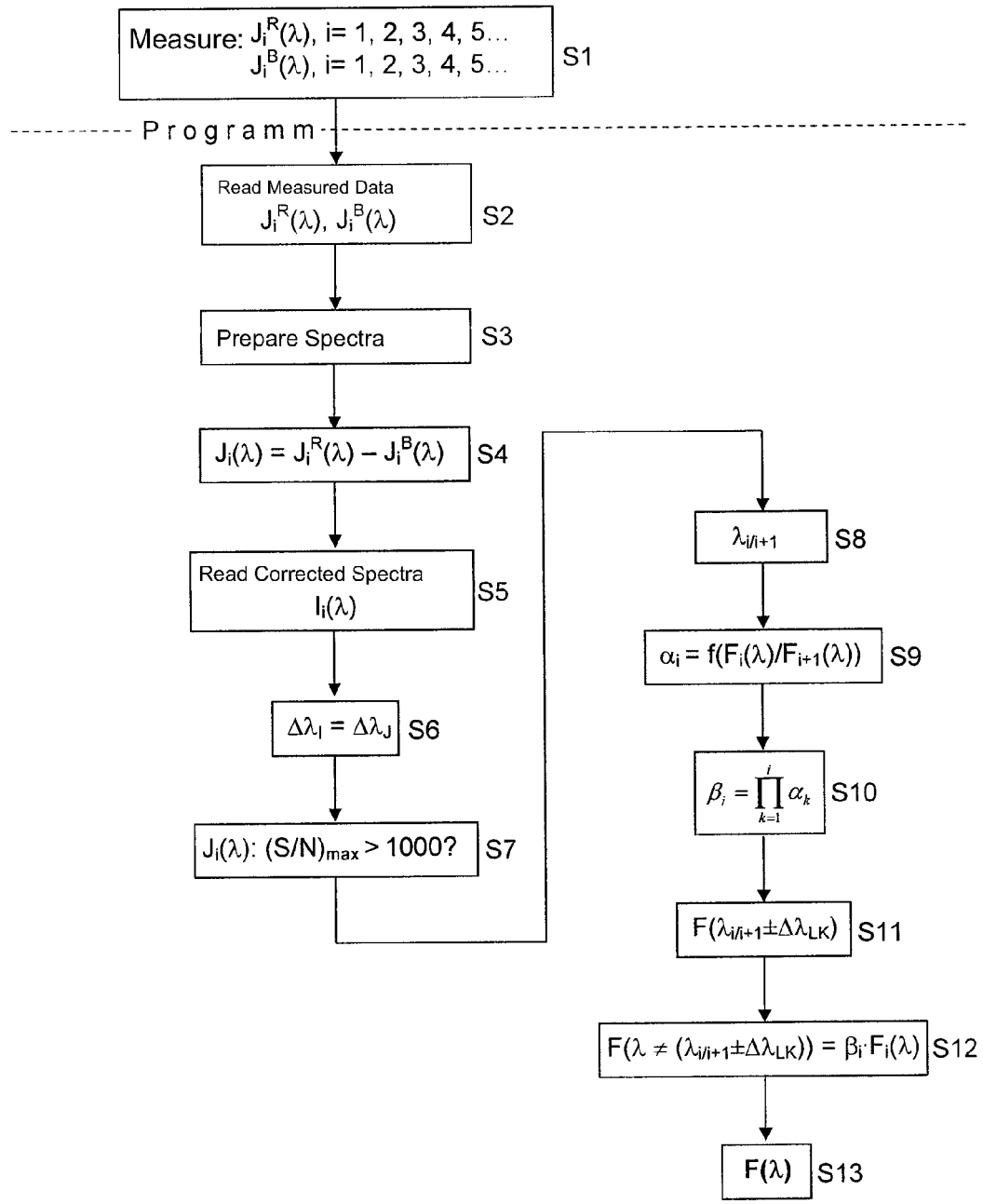
Figure 4:
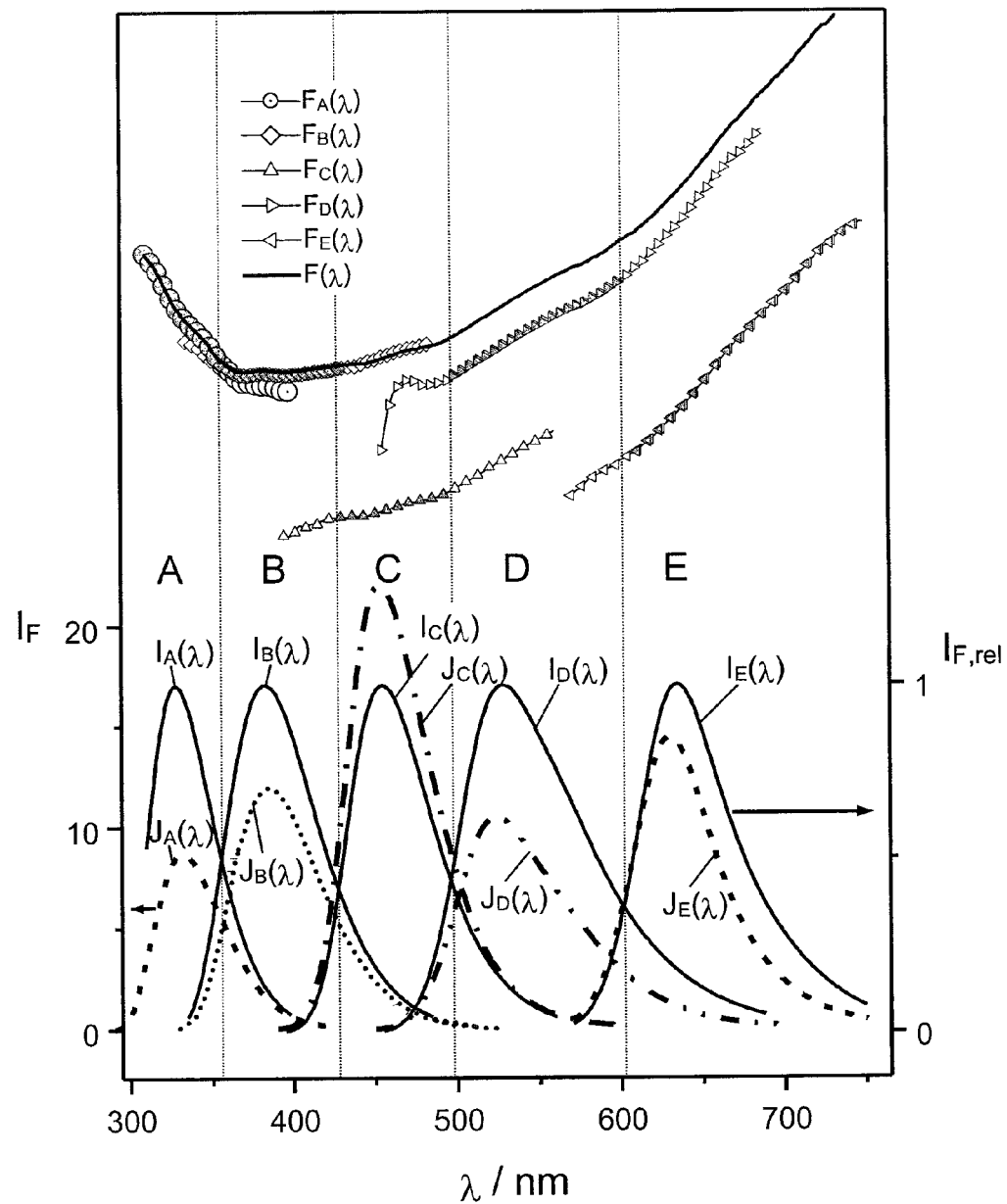
Figure 5:
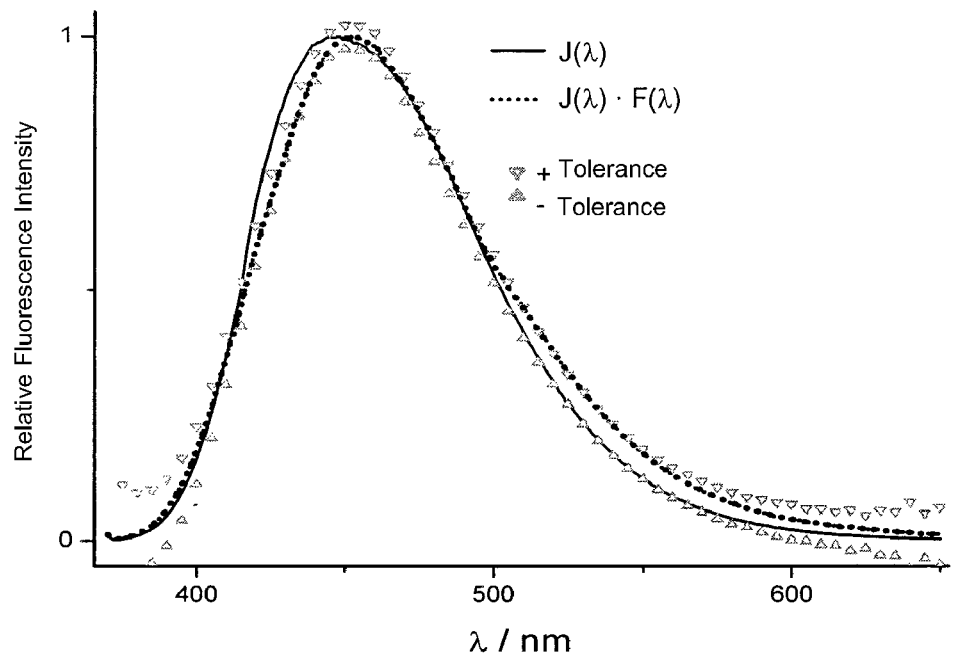
Figure 6:
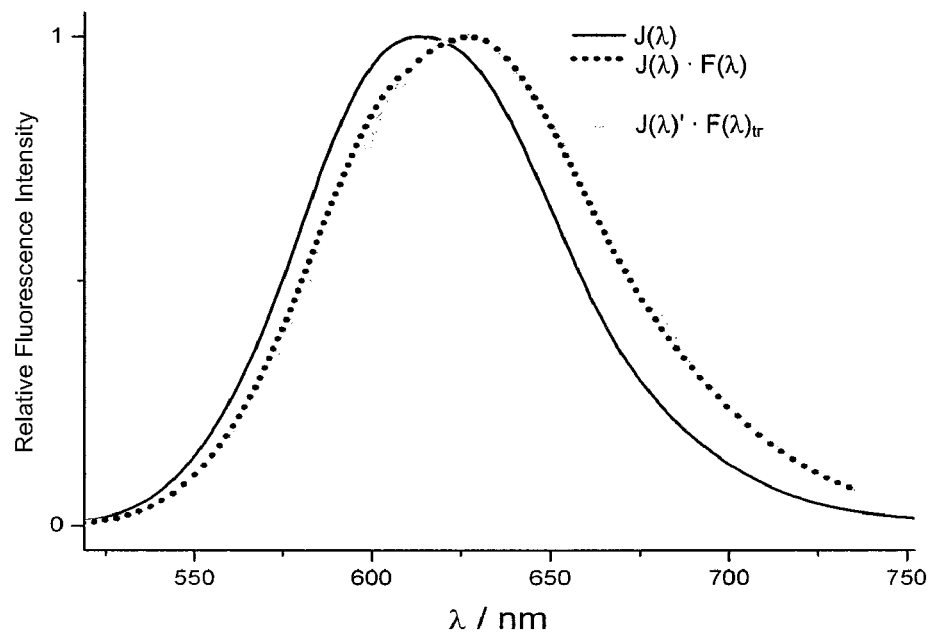

Embodiments of the invention will be described in more detail below with reference to the drawings. It is shown in:

FIG. 1 emission and excitation spectra of a set according to the invention with five emission standards;

FIG. 2 emission bands of the emission standards C and D from FIG. 1;

FIG. 3 a process flow diagram of the method of the invention for calibrating a luminescence spectrometer;

FIG. 4 diagrams of the corrected (certified) and the measured emission spectra of the dye standards A to E, as well as of the partial correction functions and of the total correction function;

FIG. 5 application of the total correction function to a fluorescence spectrum of quinine sulfate; and FIG. 6 application of the total correction function to a fluorescence spectrum of DCM.

In the present example, the emission channel of a luminescence measurement system, here a fluorescence spectrometer (fluorometer), is calibrated with a set of five fluorescence standards (emission standards) A, B, C, D and E, wherein A is a biphenyl, B a naphthalene, C and D each a coumarine, and E an oxazin derivate. The actual example includes the following dyes:

A:

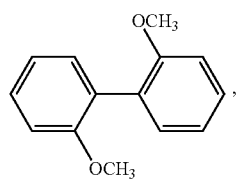

B:

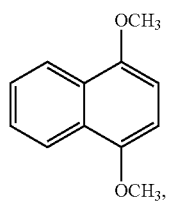

C:

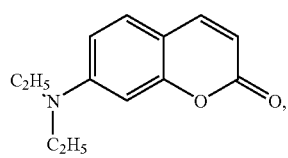

D:

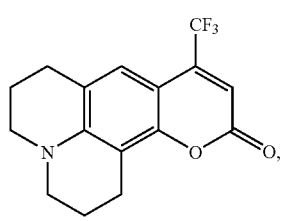

E:

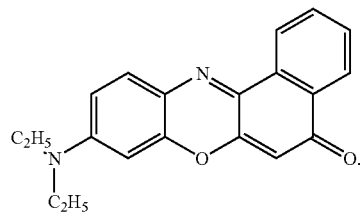

All dyes have a purity of better than 99%, and are stable over extended periods of time in solid form when stored in the dark at 4° C. in the presence of ambient oxygen.

The air-saturated solutions are sufficiently stable over extended periods of time when stored in the dark at 4° C. and do not form photo products, which absorb or emit in the spectral range intended for calibration, under the measurement and excitation conditions typically employed in photoluminescence. FIG. 1 shows the spectrally corrected and normalized emission spectrum of the emission standards A to E (top) and the corrected and normalized excitation spectrum of the five excitation standards AX to EX. As can be seen, all standard spectral bands have a broad and unstructured curve shape with only one maximum and without shoulders or discontinuities in the spectral range used for calibration. In addition, the fluorescence dyes were selected with emphasis on the greatest possible wavelength separation between the maxima of the emission spectra (Em) and the maxima of the associated absorption spectra (Abs) (Stokes shift) so as to prevent re-absorption of emitted photons due to the overlap between the EM and Abs bands. In particular, the separation for the dyes A, B, C, D, and E is approximately 5400, 4900, 4300, 4900, and 2400 $cm^{-1}$, respectively. The dyes also have a small anisotropy with $r \leqq 0.05$ (UV/vis spectral range with $\lambda \leqq 700$ nm) as well as fluorescence bands with a sufficiently small temperature dependence in a temperature range between 20° C. and 30° C.

FIG. 2 shows additional important characteristics of the selected dyes with reference to the exemplary corrected and normalized emission spectra of the fluorescence standards C and D. As can be seen, the intensity $I(\lambda_{C/D})$ of the two spectra $I_C(\lambda)$ and $I_D(\lambda)$ at their crossover point $\lambda_{C/D}$ is greater than 20% of the corresponding maximum (normalized) intensity $I_C(\lambda_{max})$ and $I_D(\lambda_{max})$. This condition is satisfied also for all the other crossover wavelengths $\lambda_{i/i+1}$. For the exemplary compounds A to E, all the crossover points have an intensity of at least 40% of the maximum intensities. The half-width $FWHM_D$ is indicated for the dye D, which according to the invention is greater than 1400 $cm^{-1}$ at least in the UV/vis spectral range for all dyes. The half-widths of the emission spectra of the exemplary compounds A to E are approximately 4250, 4400, 2850, 2890, and 1630 $cm^{-1}$, respectively.

The spectral range of the described combination of standards can be extended into the NIR spectral range by including additional dyes, for example the aforementioned merocyanine and styryl compounds according to the aforedescribed general structures 6, 7 and 8. These are subject to similar selection criteria and requirements, wherein in the spectral range at $\lambda > 700$ nm only a minimum intensity at the overlap points of, in particular, at least 12% of the maximum intensity, a half-width of in particular at least 1200 $cm^{-1}$, and an anisotropy of in particular $r \leqq 0.07$ is required.

The process flow for the calibration method according to the invention is shown in FIG. 3 in conjunction with FIG. 4. Starting at step S1 of FIG. 3, the raw emission spectra $J_i^R(\lambda)$ of the five (or more) of the aforedescribed fluorescence standards A to E included in the kit are measured with the measurement system to be calibrated. The measurement conditions at the photoluminescence measurement device—such as slit width, detector voltages, scan mode and scan speed, filters, polarizers and polarization angles, etc., are set to the parameters typically used to record fluorescence spectra and/or for which spectrally corrected luminescence spectra are required. A spectrum of blank values $J_i^B(\lambda)$ of the employed solvents is also measured under the same condition as the dye measurement.

The following user-friendly computation of a total correction function for the fluorometer is performed with a program algorithm, which performs the subsequent steps. In the following step S2, the measured raw spectra $J_i^R(\lambda)$ and the blank value spectra $J_i^B(\lambda)$ are read by the program. The program expects at least two or more measured fluorescence spectra of spectrally consecutive dyes and of the associated spectra of the blank values in an ASCII-DAT or -CVS format. The program supports spectral step intervals $\Delta\lambda(J_i)$ between the measurement points from 0.1 to 10 nm, with step widths between 0.5 and 2.0 being preferred.

In step S3, the read-in spectra are analyzed by different subroutines. The subroutines include, for example, a check of the format compatibility of the spectra and optionally a format conversion so that they can be read by the program, sorting with respect to the wavelength range and association with a dye group or with the group of blank values. In addition, in this step, all spectral ranges having intensities lower than an intensity threshold of 5%, relative to the associated maximum intensity, are clipped. Another routine associates of the measured spectra $J_i(\lambda)$ with the corresponding certified spectra $I_i(\lambda)$.

In step S4, the blank values are corrected by subtracting the solvent spectra $J_i^B(\lambda)$ from the respective measured spectra $J_i^R(\lambda)$, thereby generating the blank-value-corrected measured spectra $J_i(\lambda)$. Blank values are corrected only if the routine determines that all spectral limits ($\lambda_{Start}$ and $\lambda_{Ende}$) of the dye spectra $J_i^R(\lambda)$ are identical to those of the blank value spectra $J_i^B(\lambda)$. Otherwise, the program assumes that the blank values were already corrected by the user and enters a corresponding remark into the log file.

In step S5, the spectrally corrected and certified spectra $I_i(\lambda)$ for the five fluorescence standards together with their combined uncertainties are then read from a binary file. The spectra $I_i(\lambda)$ were measured with a traceably calibrated fluorescence spectrometer with a known measurement uncertainty, were corrected for blank values and other spectral features, and are therefore now device-independent and traceable to the radiometric primary standard "black body" or "cryo-radiometer." Because error reports were generated for all individual steps used for obtaining the fluorescence curves and for the applied certificates, a combined wavelength-dependent uncertainty or error of the measured intensities can be provided for the fluorescence standards.

In step S6, the scan step length $\Delta\lambda_I$ of the certified spectra $I_i(\lambda)$ is matched, if required, to the scan step length $\Delta\lambda_i$ of the measured spectra $J_i(\lambda)$. The missing intermediate values $I_i(\lambda_k)$ between each set of eight consecutive data points (k–3 ... k ... k+4) of the fluorescence standards are interpolated with a (smaller) spacing $\Delta\lambda_1$ by using a third-degree polynomial function (spline). The spline window is then moved sequentially across all points of each spectrum $I_i(\lambda)$. As a result, the certified spectra $I_i(\lambda)$ and the spectra $J_i(\lambda)$ corrected for the blank values have the same basis $\Delta\lambda$.

The lower part of FIG. 4 shows curves obtained by calibration on a Perkin-Elmer LS 50 B fluorometer for the blank-value-corrected emission spectra $J_i(\lambda)$ (broken lines) and the certified emission spectra $I_i(\lambda)$ after intensity normalization (continuous lines).

Thereafter, in step S7, according to FIG. 3 the signal-to-noise ratio S/N of the measured spectra $J_i(\lambda)$ is analyzed over a spectral range limited to the vicinity of the maxima. The statistical data quality is important, since the noise of the measured curves is directly transferred to the spectral correction function to be generated and therefore enters the spectral correction of each measured spectrum.

Parameters for the polynomial equations up to the $9^{th}$ degree are estimated by solving the matrices for all measured spectra $J_i(\lambda)$ in the region of their maxima (flank intensity 97 ... 100 ... 97%). For each dye i, the polynomial with the smallest deviation from the measurement data (least-square error) is assumed to be the "noise-free true curve" for the spectrum. The inverse standard deviation of the measurement points from the respective best polynomial curve is considered as a measure of the noise in the region about the corresponding band maximum. If the measure of noise is below the empirically predefined value of, for example, 1000, then a suggestion is noted in the log file, advising the user to repeat the measurement of the corresponding chromophore a number of times in order to arrive at a total correction function with a sufficiently low scatter.

The program subsequently goes to step S8, where the crossover points (more accurately: intersecting wavelengths) $\lambda_{i/i+1}$ of respective spectrally consecutive emission spectra are determined (see FIG. 2). The crossover point $\lambda_{i/i+1}^I$ (or $\lambda_{i/i+1}^J$) between two spectra is the wavelength, where the intensity of the normalized preceding (decreasing) spectrum is closest to the normalized following (increasing) spectrum, i.e., where the curves cross over. The crossover point $\lambda_{i/i+1}$ (or $\lambda_{A/B}$) is determined and averaged for respective intersecting pairs of spectra both for the measured spectra $J_i(\lambda)/J_{i+1}(\lambda)$: $\lambda_{i/i+1}^J$ (e.g., $J_A(\lambda)$, $J_B(\lambda)$) and for the corresponding certified spectra: $\lambda_{i/i+1}^I$ (e.g., $I_A(\lambda)$, $I_B(\lambda)$). The crossover point $\lambda_{i/i+1}$ of both pairs is determined as the closest rounded wavelength value which exists in all four adjacent spectra, as an average from the two pair average values $\lambda_{i/i+1}^I$ and $\lambda_{i/i+1}^J$.

In step S9, combination factors $\alpha_i$ are determined for each dye i by statistical averaging of mutually overlapping spectral ranges in the region $\pm\Delta\lambda$ about the respective crossover wavelength $\lambda_{i/i+1}$ of all four adjacent spectra $I_i(\lambda)$, $I_{i+1}(\lambda)$, $J_i(\lambda)$, and $J_{i+1}(\lambda)$ with the equations 1 to 3. In this step, the partial correction functions $F_i(\lambda)$ are implicitly computed with equation 2 by forming the quotient between the corrected spectra $I_i(\lambda)$ and the corresponding measured spectra $J_i(\lambda)$ for the individual fluorescence standards i. The curves of the (unweighted) partial correction spectra $F_A(\lambda)$ to $F_E(\lambda)$ for the standards A to E are illustrated in the top section of FIG. 4.

$$\alpha_{i+1} = \frac{\sum_\lambda \left[\frac{F_i(\lambda)}{F_{i+1}(\lambda)} \Big/ \sigma_{i/i+1}^2(\lambda)\right]}{\sum_\lambda 1/\sigma_{i/i+1}^2(\lambda)} \quad (1)$$

$$F_i(\lambda) = \frac{I_i(\lambda)}{J_i(\lambda)} \quad (2)$$

$$\sigma_{i/i+1}^2(\lambda) = \left[\frac{1}{J_i(\lambda)} + \frac{1}{J_{i+1}(\lambda)}\right] \cdot \left[\frac{F_i(\lambda)}{F_{i+1}(\lambda)}\right]^2 \quad (3)$$

For the first combination factor, $\alpha_{1=1}$. The summand in equation 1 for the combination factor $\alpha_i$ is determined only over a predefined optimized spectral overlap region $\pm\Delta\lambda_{OL}$ about the respective crossover wavelengths $\lambda_{i/i+1}$. In the present example, statistical averaging for determining $\alpha_{i+1}$ according to equation 1 is performed over a region of ±8 nm adjacent on both sides of the crossover wavelengths $\lambda_{i/i+1}$. For example, if the crossover point $\lambda_{A/B}$ is located at 350 nm, then $\alpha_B$ is determined by statistical averaging of the partial correction functions $F_A(\lambda)$ and $F_B(\lambda)$ over the spectral range 350±8 nm.

In step S10, the connection factors $\beta_i$ are determined for each fluorescence standard i according to equation 4 by multiplying all spectrally preceding combination factors $\alpha_i$. $\alpha_1 \equiv 1$ requires $\beta_1 = 1$.

$$\beta_i = \prod_{k=1}^{i} \alpha_k \tag{4}$$

Finally, in steps S11 to S13, the total correction function $F(\lambda)$ is computed. Although according to the employed program algorithm these steps do not represent separate steps (but rather a single computing step consisting in the summation according to equation 5), steps S11 to S13 are shown in FIG. 3 as separate steps for a better understanding. Accordingly, in step S11, the values of the function $F(\lambda)$ are initially determined in a predefinable combination region $\lambda_{i/i+1} \pm \Delta\lambda_{LK}$ about the respective crossover points $\lambda_{i/i+1}$ according to equations 5 and 6. In the combination region $\lambda_{i/i+1} \pm \Delta\lambda_{LK}$, the overlapping partial correction functions $F_i(\lambda)$, which are weighted by $\beta_i$, are statistically averaged. In the present example, equation 5 is applied only to the crossover wavelengths $\lambda_{i/i+1}$ determined in step S8, i.e., $\Delta\lambda_{LK} = 0$, according to a predetermined execution mode of the program.

$$F(\lambda) = \frac{\sum_{i=1}^{N} \beta_i \cdot F_i(\lambda)/\sigma^2(\lambda)}{\sum_{i=1}^{N} 1/\sigma^2(\lambda)} \tag{5}$$

with $$\sigma^2(\lambda) = \frac{[\beta_i F_i(\lambda)]^2}{J_i(\lambda)}. \tag{6}$$

All other points of the correction function $F(\lambda)$, i.e., in the regions $\lambda \neq \lambda_{i/i+1} \pm \Delta\lambda_{LK}$, are according to the predefined execution mode of the program not determined in step S12, but are simply computed according to equation 7. (This is the same as a summing in equation 5 over only one i). In other words, the total correction function $F(\lambda)$ outside the combination regions $\lambda_{i/i+1} \pm \Delta\lambda_{LK}$, in particular for all wavelengths outside the crossover points $\lambda_{i/i+1}$, corresponds to the partial correction functions $F_i(\lambda)$ weighted with the factors $\beta_i$ determined for these functions $F_i(\lambda)$.

$$F(\lambda) = \beta_i \cdot F_i(\lambda) \tag{7}$$

The effective range of the equations 5 and 6 in the program can optionally be extended to broader spectral combination regions $\lambda_{i/i+1} \pm \Delta\lambda_{LK}$ about the crossover wavelengths through user input of corresponding control variables. The exemplary dataset in FIG. 4 (top) shows that this is frequently not advantageous, since the partial correction functions $F_C(\lambda)$ and $F_D(\lambda)$ significantly deviate at their respective starting regions and the partial quotient $F_E(\lambda)$ significantly deviates at the end from otherwise continuous curve shapes. The program was therefore used in default mode for the emission correction function $F(\lambda)$, which is also shown at the top of FIG. 4. Stated differently, only the filled parts of the individual quotients $F_i(\lambda)$ between the crossover wavelengths $\lambda_{i/i+1}$ were computed with the connection factors $\beta_i$ according to FIG. 7. An average between the two adjacent partial quotients was formed at the intersections $\lambda_{i/i+1}$ according to equation 5, yielding the total correction function $F(\lambda)$ (black line), which is smooth and continuous. Because $\alpha_1 = 1$ and $\beta_1 = 1$, $F(\lambda)$ corresponds up to the first crossover point $\lambda_{A/B}$ to the partial correction function $F_A(\lambda)$ weighted with $\beta_A$.

In step S13, the values of the concatenated total correction function $F(\lambda)$ are outputted as an ASCII table in the file "CorrF.TXT", and all actions and error messages of the program are documented in a log file "LINKLOG#.TXT."

All spectra measured with a luminescent spectrometer calibrated in this manner and with the calibration settings are spectrally corrected, after subtraction of corresponding blank value spectra, by simple multiplication with a correction function $F(\lambda)$. Values of the measured spectrum and the spectral correction function $F(\lambda)$ must only be multiplied with each other, if they are associated with the same wavelength, i.e., the same base $\Delta\lambda$. In this way, traceable, spectrally corrected luminescent spectra expressed in relative intensity units can be obtained.

The aforedescribed example is related to the generation of a total correction function for the emission by using emission standards. A spectral excitation correction function can be obtained by measuring a set of excitation standards with a luminescence spectrometer in the same manner and by computing the obtained excitation spectra with a dataset for the spectrally corrected (certified) excitation spectra of the fluorescence standards according to the program flow in FIG. 3.

FIG. 5 shows in form of an example, how the total correction function $F(\lambda)$ obtained according to FIGS. 3 and 4 can be applied to the fluorescence of quinine sulfate. The continuous curve shows the spectrally uncorrected emission spectrum $J(\lambda)$ measured with a fluorometer (SPEX Fluorolog) within excitation wavelengths of 348 nm. The spectrum was, however, corrected for blank values. The spectrally corrected emission spectrum (dotted curve) is obtained after multiplication with the emission correction function $F(\lambda)$ obtained for the fluorometer by using the fluorescence standard kit according to the invention. Unlike the spectrally uncorrected spectrum, the spectrally corrected emission spectrum lies in all regions below the error limits defined by NIST (gray triangles).

FIG. 6 clearly shows the potential impact of the spectral correction on the spectral position on the fluorescence maximum. The raw emission spectrum $J(\lambda)$ of DCM in acetone nitrile was recorded on a fluorometer LS 50B from the company Perkin Elmer. The spectrally corrected spectrum (dotted curve), which is bathochrome shifted by 11 nm, is obtained by applying the spectral emission correction (multiplication of the measured raw spectrum $J(\lambda)$ with the emission correction function $F(\lambda)$. This curve deviates only slightly from the spectrum measured with a fluorometer SLM 8100, which had been spectrally corrected with an emission correction function $F(\lambda)_{tr}$ produced with a radiance transfer standard (gray curve).

LIST OF REFERENCE SYMBOLS/ABBREVIATIONS i consecutive numbering of a fluorescence standard in the kit with $1 \leq i \leq N$ $I_i(\lambda)$ spectrally corrected (certified) fluorescence spectrum of the fluorescence standard i $J_i(\lambda)$ measured, blank value corrected fluorescence spectrum
$F_i(\lambda)$ partial correction function of the fluorescence standard i
$F(\lambda)$ total correction function
$\lambda_{i/i+1}$ crossover wavelengths of consecutive spectra of the $i^{th}$ and the $(i+1)^{th}$ standard
$\alpha_i$ combination factor of adjacent partial correction functions
$\beta_i$ connection factor
$\lambda_{i/i+1} \pm \Delta\lambda_{OL}$ spectral overlap region about the crossover wavelengths
$\lambda_{i/i+1} \pm \Delta\lambda_{LK}$ spectral combination region about the crossover wavelengths

The invention claimed is:

1. A kit for calibration of a photoluminescence measurement system, the kit comprising:
(a) a plurality of fluorescence standards (i) comprising at least one of
a biphenyl derivate according to the general formula (1)

(1)

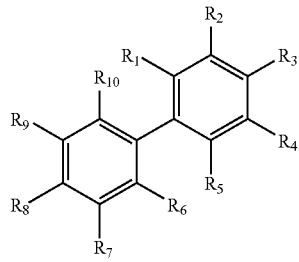

wherein $R_1$ and $R_6$ each represent an alkoxy moiety, and the remaining moieties $R_2$-$R_5$ and $R_7$-$R_{10}$ independently represent a hydrogen or an alkyl moiety, wherein the alkoxy and alkyl moieties independently are cyclic or acyclic, branched or linear;
a naphthalene derivate according to the general formula (2)

(2)

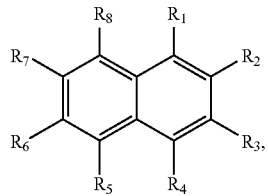

wherein the moieties $R_1$ to $R_8$ independently represent a hydrogen or an alkoxy moiety, or partially in combination with each other an anellated, saturated, hetero- or homo-nuclear ring;
a 3H-phenoxazin-5-on derivate according to the general formula (5)

(5)

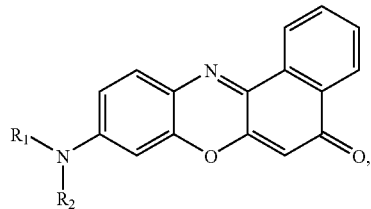

wherein the moieties $R_1$ and $R_2$ independently represent an unsubstituted or a substituted, branched or linear alkyl moiety;
a hemicyanin derivate according to the general formula (7)

(7)

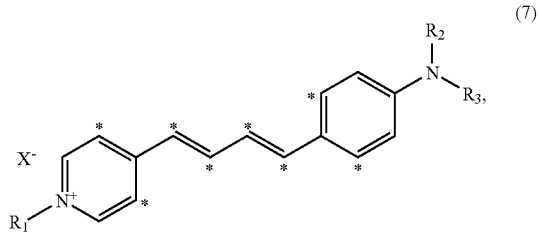

wherein $R_1$ to $R_3$ independently represent an unsubstituted or a substituted, branched or linear alkyl moiety, $X^-$ an arbitrary anion, and the C atoms designated with an asterisk can be independently bridged by a saturated C5 or C6 ring;
a hemicyanin derivate according to the general formula (8)

(8)

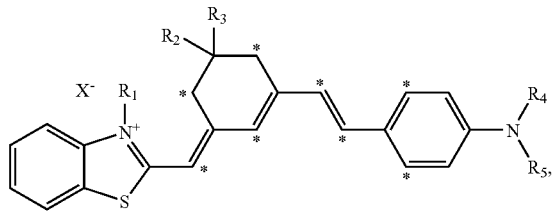

wherein $R_1$ to $R_5$ independently represent a hydrogen moiety or an unsubstituted or a substituted, branched or linear alkyl moiety, $X^-$ an arbitrary anion, and the C atoms designated with an asterisk independently can be bridged by a saturated C5 or C6 ring;
a p-terphenyl according to the general formula (9)

(9)

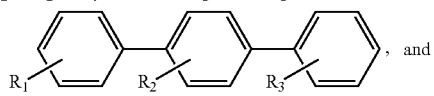, and wherein $R_1$ to $R_3$ independently represent hydrogen, or an alkyl or alkoxy moiety;
a 1,3,4-oxadiazol derivate according to the general formula (10)

(10)

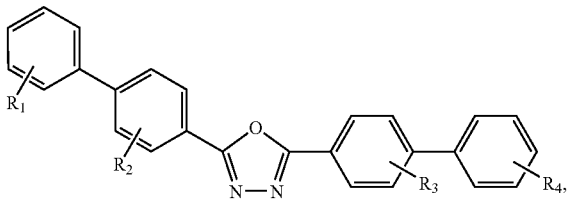

wherein $R_1$ to $R_4$ independently represent hydrogen, or an alkyl or alkoxy moiety; and
(b) corrected fluorescence spectra ($I_i(\lambda)$) of the fluorescence standards (i) in computer-readable form and/or in a form to be downloaded from an Internet page,
wherein the fluorescence standards (i) meet the following criteria:
cover a predefined spectral range in such a way that fluorescence bands of the corrected fluorescence spectra ($I_i(\lambda)$) have in the vis/NIR spectral range with a wavelength less than or equal to 700 nm at least a minimal predefined intensity at their overlapping wavelengths ($\lambda_{i/i+1}$) of at least 20% of a corresponding maximum band intensity, fluorescence bands have each a half-width of at least 1400 cm$^{-1}$ and fluorescence bands each have an unstructured band curve without a shoulder and with only one respective maximum in a relevant spectral range at a spectral resolution of 1 nm.

2. The kit according to claim 1, wherein the plurality of fluorescence standards (i) further comprise:

a coumarine derivate according to the general formula (3)

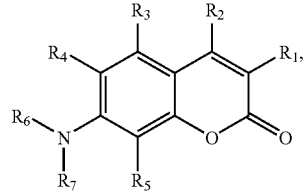

(3)

wherein the moieties $R_1$ to $R_7$ independently represent a hydrogen moiety or an unsubstituted or a substituted alkyl moiety, or partially in combination with each other an anellated, saturated homo-nuclear ring.

3. The kit according to claim 2, wherein, for the general formula (3), $R_1$ and $R_2$ independently represent a hydrogen moiety or an unsubstituted or a substituted alkyl moiety, or an anellated, saturated homo-nuclear ring, $R_3$ to $R_5$ each represent a hydrogen moiety, and $R_6$ and $R_7$ independently represent a hydrogen moiety or an alkyl moiety.

4. The kit according to claim 2, wherein, for the general formula (3), $R_1$ to $R_5$ each represent a hydrogen moiety and $R_6$ and $R_7$ each represent an ethyl group.

5. The kit according to claim 1, wherein the plurality of fluorescence standards (i) further comprise:

a coumarine derivate according to the general formula (4)

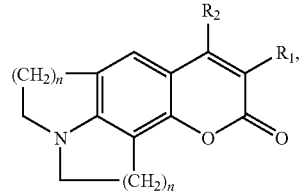

(4)

wherein the moieties $R_1$ and $R_2$ independently represent a hydrogen moiety or an unsubstituted or a substituted alkyl moiety, or in combination with each other an anellated, saturated homo-nuclear ring, with n=1 or 2.

6. The kit according to claim 5, wherein, for the general formula (4), $R_1$ represents a hydrogen moiety and $R_2$ represents an unsubstituted or a substituted alkyl moiety, with each n=1 or 2.

7. The kit according to claim 5, wherein, for the general formula (4), $R_1$ represents a hydrogen moiety and $R_2$ represents a trifluoromethyl moiety, with each n=2.

8. The kit according to claim 1, wherein the plurality of fluorescence standards (i) further comprise:

a styryl derivate according to general formula (6)

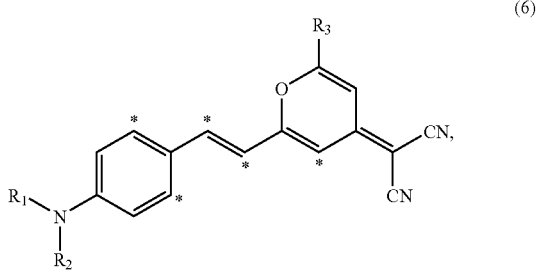

(6)

wherein $R_1$ and $R_2$ independently represent an unsubstituted or a substituted, branched or linear alkyl moiety, $R_3$ represents a hydrogen moiety or an unsubstituted or a substituted, branched or linear alkyl moiety, and the C atoms designated with an asterisk can be independently bridged by a saturated C5 or C6 ring.

9. The kit according to claim 8, wherein, for the general formula (6), $R_1$ to $R_3$ are each a methyl moiety, and no bridging C5 or C6 ring is present.

* * * * *